(12) United States Patent
Huang et al.

(10) Patent No.: US 8,002,874 B2
(45) Date of Patent: Aug. 23, 2011

(54) LIQUID-PHASE AND VAPOR-PHASE DEHYDRATION OF ORGANIC/WATER SOLUTIONS

(75) Inventors: Yu Huang, Palo Alto, CA (US); Jennifer Ly, San Jose, CA (US); Tiem Aldajani, San Jose, CA (US); Richard W. Baker, Palo Alto, CA (US)

(73) Assignee: Membrane Technology and Research, Inc., Menlo Park, CA (US)

( * ) Notice: Subject to any disclaimer, the term of this patent is extended or adjusted under 35 U.S.C. 154(b) by 569 days.

(21) Appl. No.: 11/715,245

(22) Filed: Mar. 6, 2007

(65) Prior Publication Data

US 2008/0216649 A1   Sep. 11, 2008

(51) Int. Cl.
*B01D 53/22* (2006.01)
(52) U.S. Cl. ...................... 95/50; 95/52; 210/640; 96/14
(58) Field of Classification Search ................. 95/50, 52; 96/4, 14, 13; 210/640
See application file for complete search history.

(56) References Cited

U.S. PATENT DOCUMENTS

| | | | |
|---|---|---|---|
| 3,735,558 A | 5/1973 | Skarstrom et al. | |
| 3,950,247 A | 4/1976 | Chiang et al. | |
| 5,051,114 A | 9/1991 | Nemser et al. | |
| 5,387,378 A | 2/1995 | Pintauro et al. | |
| 6,316,684 B1 | 11/2001 | Pinnau et al. | |
| 6,361,582 B1 | 3/2002 | Pinnau et al. | |
| 6,361,583 B1 | 3/2002 | Pinnau et al. | |
| 6,406,517 B1 | 6/2002 | Avery et al. | |
| 6,572,679 B2 | 6/2003 | Baker et al. | |
| 2002/0170430 A1 | 11/2002 | Baker | |
| 2003/0233934 A1* | 12/2003 | Wijmans et al. | 95/46 |
| 2004/0000521 A1* | 1/2004 | Vane et al. | 210/640 |
| 2004/0003714 A1* | 1/2004 | Bikson et al. | 95/45 |
| 2004/0173529 A1 | 9/2004 | Da Costa et al. | |
| 2006/0000777 A1* | 1/2006 | Da Costa et al. | 210/640 |
| 2007/0031954 A1 | 2/2007 | Mairal et al. | |

FOREIGN PATENT DOCUMENTS

| | | |
|---|---|---|
| EP | 0303298 | 2/1989 |
| EP | 0649676 | 4/1995 |
| WO | WO90/15662 | 12/1990 |

OTHER PUBLICATIONS

D. W. van Krevelan, *Properties of Polymers*, 3$^{rd}$ Edition, Elsevier, Amsterdam, 1990, pp. 71-76.
Chapman et al. (2008) "Membranes for the dehydration of solvents by pervaporation", *Journal of Membrane Science* 318 pp. 5-37.

* cited by examiner

*Primary Examiner* — Duane Smith
*Assistant Examiner* — Tiffany N Palmer
(74) *Attorney, Agent, or Firm* — Weaver Austin Villeneuve & Sampson LLP

(57) ABSTRACT

Processes for dehydrating an organic/water solution by pervaporation or vapor separation using fluorinated membranes. The processes are particularly useful for treating mixtures containing light organic components, such as ethanol, isopropanol or acetic acid.

26 Claims, 6 Drawing Sheets

LIQUID-PHASE AND VAPOR-PHASE DEHYDRATION OF ORGANIC/WATER SOLUTIONS

STATEMENT REGARDING FEDERALLY SPONSORED RESEARCH

This invention was made in party with Government support under SBIR award number DE-FG02-04ER84001, awarded by the Department of Energy. The Government has certain rights in this invention.

FIELD OF THE INVENTION

The invention relates to the dehydration of organic/water solutions by means of separation membranes. The separation is performed under pervaporation conditions, in which the feed stream is in the liquid phase and the membrane permeate is in the vapor phase, or under vapor-phase conditions, in which the feed and permeate are in the vapor phase.

BACKGROUND OF THE INVENTION

The production of fuel grade ethanol from renewable resources is expected to increase. Presently, many bioethanol plants in the U.S. use corn as the feedstock. Fermentation of lignocellulose to produce bioethanol is not currently economical. However, if research on this use of lignocellulose develops successfully, there will be an even larger increase in bioethanol production.

A major drawback to more economical use of bioethanol as a fuel is the energy used to grow the feedstock, to ferment it, and to separate a dry ethanol product from the fermentation broth. In this regard, the development of a lower energy ethanol separation (dehydration) process would be of considerable interest and use to bioethanol producers.

Dehydration of other organic liquids is also of economic importance. Isopropanol is widely used in the electronics industry and in the production of precision metal parts as a drying agent. The component to be dried is dipped or sprayed with anhydrous isopropanol, which removes any water, after which the component is dried. The isopropanol solvent eventually becomes contaminated with water and when it reaches about 10-30% weight of water it must be replaced. It would be economical to recover the isopropanol rather than disposing of it as a hazardous waste, as is presently done. Distillation of isopropanol/water is not economically feasible since it forms an azeotrope at 87% isopropanol-13% water.

Another important organic liquid is acetic acid, the most widely used organic acid. Its primary industrial uses are for the production of vinyl acetate monomer and as a solvent in making terephthalic acid. In production of terephthalic acid, large aqueous acetic acid streams are produced from which acetic acid must be recovered and a water stream produced that is sufficiently decontaminated to be properly discharged into the environment. An energy and cost-saving method for producing a dehydrated acetic acid stream suitable for recycling along with waste water stream suitable for discharging would be of considerable economic interest.

While there are some commercially available membranes capable of dehydrating organic compounds by pervaporation, these membranes are hydrophilic, in that they swell significantly, or even dissolve, in an aqueous environment. They start to lose their separation properties, and are, therefore, unusable, even at water concentrations of just a few percent. The problem is exacerbated if the feed solution is hot. Unfortunately, many economically important organic solutions, such as those mentioned above, are not amenable to treatment by pervaporation for this reason.

There is thus a need in several industrial applications for more economical methods of dehydrating organic/water mixtures.

SUMMARY OF THE DISCLOSURE

The invention is directed to processes for dehydrating organic/water solutions by vapor-phase or liquid-phase membrane separation.

In one embodiment, the separation is carried out by running a feed stream of the organic/water solution across a membrane under pervaporation conditions. By pervaporation conditions, we mean that the vapor pressure of the desired faster permeating component is maintained at a lower level on the permeate side than the feed side, and the pressure on the permeate side is such that the permeate is in the gas phase as it emerges from the membrane. The process results, therefore, in a permeate stream enriched in one component, in this case water, and a residue liquid stream depleted in that component.

In another embodiment, the separation is carried out by running the feed stream across the membrane as a vapor, and by providing a difference in partial pressure between components on the feed and permeate sides. The process again results in a permeate vapor stream enriched in one component, in this case water, and a residue vapor stream depleted in that component.

The membranes used in the process of the invention have selective layers made from a hydrophobic fluorinated glassy polymer or copolymer. This polymer determines the membrane selectivity.

The polymer is characterized by having repeating units of a fluorinated, cyclic structure, the fluorinated ring having at least five members, where the fluorinated ring is preferably in the polymer backbone. Preferably, the polymer is formed from a monomer selected from the group consisting of fluorinated dioxoles, fluorinated dioxolanes and fluorinated cyclically polymerizable alkyl ethers.

The polymer is further characterized by its hydrophobic nature. To be useful in the invention, the selective layer polymer should exhibit only modest swelling when exposed to significant concentrations of water, especially at high temperature.

The process may be characterized in terms of having membrane selectivity of water to the organic compound of at least about 30 and a water permeance of at least about 500 gpu when challenged at 75° C. with a liquid mixture of 90 wt % ethanol/10 wt % water at a permeate pressure of less than 10 torr.

The fluorinated polymer is preferably heavily fluorinated, by which we mean having a fluorine:carbon ratio of atoms in the polymer of at least about 1:1. Most preferably, the polymer is perfluorinated.

In one embodiment, the dehydration process of the invention includes the following steps:

(a) providing a membrane having a feed side and a permeate side, the membrane having a selective layer comprising a polymer with a repeat unit of a hydrophobic fluorinated cyclic structure of an at least 5-member ring;

(b) passing a feed solution comprising at least 1 wt % water and a liquid organic compound across the feed side under pervaporation conditions;

(c) withdrawing from the feed side a dehydrated solution having a water content lower than that of the feed solution;

(d) withdrawing from the permeate side a permeate vapor having a higher water content than the feed solution.

In particular, the pervaporation conditions in step (b) may include providing the feed solution to the membrane at a temperature in the range of about 70 to 120° C.

In another embodiment the dehydration process includes the following steps:

(a) providing a membrane having a feed side and a permeate side, the membrane having a selective layer comprising a polymer with a repeat unit of a hydrophobic fluorinated cyclic structure of an at least 5-member ring;

(b) passing a feed vapor comprising at least 1 wt % water vapor and a vaporized organic compound across the feed side;

(c) providing a vapor pressure driving force for transmembrane permeation;

(d) withdrawing from the feed side a dehydrated vapor having a water content lower than that of the feed solution;

(e) withdrawing from the permeate side a permeate vapor enriched having a higher water content than the feed solution.

In particular, the water vapor and vaporized organic compound may be provided to the membrane in step (b) at a temperature in the range of about 70 to 130° C.

In either embodiment, there may be further processing by passing at least a portion of a stream chosen from the permeate vapor and the dehydrated liquid or vapor stream to additional separation treatment. Any of the permeate or residue streams in the vapor phase may optionally be condensed. At least a portion of the permeate vapor is often condensed to provide or contribute to the driving force for transmembrane permeation.

Particularly preferred materials for the selective layer of the membrane used to carry out the process of the invention are amorphous homopolymers of perfluorinated dioxoles, dioxolanes or cyclic alkyl ethers, or copolymers of these with tetrafluoroethylene. One class of preferred materials are copolymers having the structures:

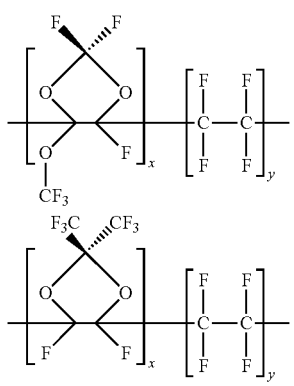

where x and y represent the relative proportions of the dioxole and the tetrafluoroethylene blocks, such that x+y=1.

A second class of preferred material has the structure:

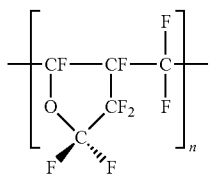

where n is a positive integer.

These preferred polymer materials are amorphous glassy materials with glass transition temperatures in the range of 100 to 250° C. The exceptional permeation properties of these membranes are derived from their structure. The materials are amorphous, glassy, highly fluorinated and without any ionic groups that would render the membranes hydrophilic or provide an affinity for other polar materials. As a result, they are not swollen to any significant extent by polar solvents, such as ethanol, isopropanol, butanol, acetone, acetic acid and water. This low sorption, together with the intrinsic resistance to hydrolysis of fluoro polymers, makes these polymers chemically stable, even in hot organic/water mixtures that contain 20 wt % water or more, or are even predominantly aqueous.

These properties contrast with polymers, including crosslinked polyvinyl alcohol (PVA); polyvinylpyrrolidone (PVP); ion-exchange polymers, such as Nafion® and other sulfonated materials; and chitosan, that have previously been used for pervaporation membranes to remove small amounts of water from organic solutions.

We have found that membranes formed from fluorinated polymers as characterized above can operate satisfactorily as pervaporation membranes for dehydration of organic/water solutions. In other words, the membranes can be used to carry out dehydration under conditions in which the feed stream is essentially completely in the liquid phase, and hence the membrane is in continuous contact with liquid organic/water solutions throughout the duration of the dehydration process.

We have also found that membranes formed from fluorinated polymers as characterized above can operate satisfactorily as vapor-phase separation membranes for dehydration of organic/water solutions. In other words, the membranes can be used to carry out dehydration under conditions in which the feed stream is essentially completely in the vapor phase, and hence the membrane is in continuous contact with organic/water vapors throughout the duration of the dehydration process.

Because the preferred polymers are glassy and rigid, an unsupported film of the polymer may be usable in principle as a single-layer gas separation membrane. However, such a film will normally be far too thick to yield acceptable transmembrane flux, and in practice, the separation membrane usually comprises a very thin selective layer that forms part of a thicker structure, such as an asymmetric membrane or a composite membrane. Composite membranes are preferred.

The making of these types of membranes is well known in the art. If the membrane is a composite membrane, the support layer may optionally be made from a fluorinated polymer also, making the membrane a totally fluorinated structure and enhancing chemical resistance. A useful support layer may comprise microporous polyvinylidene fluoride (PVDF). The membrane may take any form, such as hollow fiber, which may be potted in cylindrical bundles, or flat sheets, which may be mounted in plate-and-frame modules or formed into spiral-wound modules.

The driving force for transmembrane permeation is the difference between the vapor pressure of the feed liquid or vapor and the vapor pressure on the permeate side. This pressure difference can be generated in a variety of ways, for example, by heating the feed liquid, compressing the feed vapor and/or maintaining lower pressure or a partial vacuum on the permeate side.

The invention can dehydrate water/organic solutions of any composition, from those that contain only small amounts of water, such as 1 wt % or less, to those that contain only small amounts of organics, such as 1 wt % or less. The invention is particularly useful for dehydrating organic solutions that contain more than 1 wt % water, such as 5 wt % water, 10 wt % water, 20 wt % water or more, which cannot be treated using conventional membranes.

The membranes and processes of the invention are particularly useful for dehydration of organic compounds such as alcohols, ketones, aldehydes, esters or acids, in which water is readily soluble, or that are miscible with water over a wide concentration range. By readily soluble it is meant that water has a solubility of at least about 10 wt % at room temperature and pressure. The invention is especially useful for dehydration of C1 to C6 alcohols, such as ethanol, isopropanol and butanol.

The membrane separation process may be configured in many possible ways, and may include a single membrane unit or an array of two or more units in series or cascade arrangements, as is familiar to those of skill in the art.

The processes of the invention also include combinations of the membrane separation process defined above with other separation processes, such as adsorption, absorption, distillation, condensation or other types of membrane separation.

It is to be understood that the above summary and the following detailed description are intended to explain and illustrate the invention without restricting its scope.

DETAILED DESCRIPTION

Figure 1:
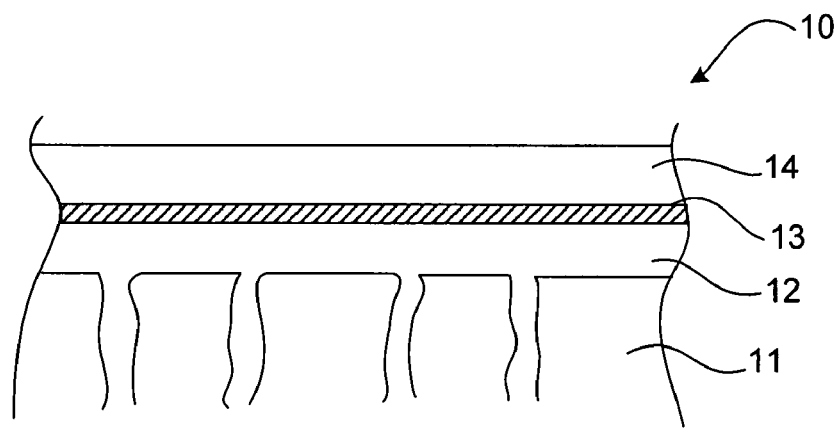
FIG. 1 is an illustration of an embodiment of a membrane for use in accordance with the invention.

The term gas as used herein means a gas or a vapor.

The terms hydrocarbon and organic vapor or organic compound are used interchangeably herein, and include, but are not limited to, saturated and unsaturated compounds of hydrogen and carbon atoms in straight chain, branched chain and cyclic configurations, including aromatic configurations, as well as compounds containing oxygen, nitrogen, halogen or other atoms.

The term separation factor refers to the overall separation factor achieved by the process. The separation factor is equal to the product of the separation achieved by evaporation of the liquid and the selectively achieved by selective permeation through the membrane.

The terms water/organic and organic/water solution and mixture used herein refer to mixtures of one or more organic compounds and water that are liquid at room temperature and pressure.

All liquid mixture percentages herein are by weight unless otherwise stated. Gas or vapor mixture percentages are by volume unless otherwise stated.

The invention is a process for dehydrating an organic/water solution.

The separation is carried out by running a liquid or vapor stream of the water/organic mixture across a membrane that is selective for water to be separated over the organic component of the mixture. The process results, therefore, in a permeate stream enriched in water and a residue stream depleted of water, i.e., dehydrated.

In one embodiment, the process is performed under pervaporation conditions, as explained in more detail below, so that the feed is in the liquid phase and the permeate stream is in the gas or vapor phase.

In another embodiment, the process is performed in the gas phase so that the feed and permeate streams are both in the gas phase.

The process of the invention can be used to dehydrate essentially any water/organic solution. We believe the process of the invention is of particular value in dehydrating solutions in which the organic component is in the range C1-C6, that is, has 1 to 6 carbon atoms, or where the solubility of water in the organic liquid at room temperature and pressure is at least about 10 wt %.

By way of example, the process of the invention is particularly useful for separating water from the following: alcohols, ketones, aldehydes, organic acids and esters, including:

ethanol, particularly bioethanol produced from natural sources (C2)
isopropanol (C3)
butanol (C4)
acetone (C3)
acetic acid (C2)
formaldehyde (C1)
ABE mixtures (acetone-butanol-ethanol)

One or multiple organic compounds may be present in the solution to be dehydrated. A common example of an organic mixture to be treated is ABE, an acetone-butanol-ethanol mixture produced, for example, by fermentation using clostridium organisms, and used as a source of biobutanol and other valuable chemicals. The processes are characterized in terms of the material used for the selective layer of the membrane or by a preferred target performance of the membrane under set operating conditions.

In the first aspect, the selective layer is made from a fluorinated glassy polymer, characterized by having repeating units of a cyclic structure, the ring having at least five members and being at least partially fluorinated. Generally, but not necessarily, the fluorinated ring is in the polymer backbone.

The ring structure within the repeat units may be aromatic or non-aromatic, and may contain other atoms than carbon, such as oxygen atoms.

In the second aspect, the process may be characterized by target separation characteristics. Preferably, the membranes provide a membrane selectivity of water to the organic compound of at least about 30 and a water permeance of at least about 500 gpu when challenged at 75° C. with a liquid mixture of 10 wt % water/90 wt % ethanol at a permeate pressure of less than 10 torr.

It should be understood that this characterization does not limit the process of the invention in this aspect to dehydration or to specific operating conditions. Membranes that meet this selectivity criterion may be operated at other temperatures and pressures.

It should further be understood that the definition relies on the selectivity, which is a membrane property, not the separation factor, which is a process attribute.

When characterized according to either aspect, the polymer is typically heavily fluorinated, by which we mean having a fluorine:carbon ratio of atoms in the polymer preferably of at least about 1:1, and more preferably is perfluorinated.

A measure of the chemically stable and hydrophobic nature of the polymer is its resistance to swelling when exposed to water. This may be measured in a very simple manner by weighing a film of the pure polymer, then immersing the film in boiling water for a period. When the film is removed from the water, it is weighed immediately, and again after the film has been allowed to dry out and reach a stable weight.

The selective layer of our membrane should be made from a polymer that is sufficiently stable in the presence of water that a film of the polymer immersed in water at 100° C. for 24 hours at atmospheric pressure will experience a weight change of no more than about 10 wt %, and more preferably no more than about 5 wt %. If the film is removed from the boiling water and weighed immediately, its weight will have increased compared with the original weight because of the presence of sorbed water. This weight increase should be no more than 10 wt % and preferably no more than 5 wt %. After the film is dried out and the weight has stabilized, it is weighed again. If the film has suffered degradation as a result of the water exposure test, the weight may have decreased. The weight loss compared with the original weight should be no more than 10 wt % and preferably no more than 5 wt %.

Conventional materials used for dehydration membranes, including PVA, PVP, chitosan and fluorinated ion-exchange materials will typically fail this test, as will many materials that are insufficiently fluorinated or that do not have the defined ring structure.

Since the polymers used for the selective layer need to remain rigid and glassy during operation, they should have glass transition temperatures comfortably above temperatures to which they are typically exposed during the process. Polymers with glass transition temperature above about 100° C. are preferred, therefore, and, subject also to the other requirements and preferences above, the higher the glass transition temperature, in other words, the more rigid the polymer, the more preferred it is.

The polymers should preferably take amorphous, rather than crystalline form, because crystalline polymers are typically essentially insoluble and thus render membrane formation difficult, as well as exhibiting low gas permeability. The degree of crystallinity of the polymer should therefore normally be less than 50%, and preferably less than 20%, and even more preferably less than 10%.

Normally, and preferably, the polymer is non-ionic, that is, does not contain charged groups such as are incorporated into ion-exchange polymers. Polymers containing ionic groups are insufficiently stable in the presence of water, and fail the swellability test described above.

The selectivity of the membranes should be determined principally by the selective properties of the polymer. In other words, the polymer as used for the selective layer should not contain any fillers, such as inorganic particles, that alter the polymer permeation properties. It is believed that the use of filled polymers, such as taught in U.S. Pat. No. 6,316,684, increases the free volume within the polymer and may raise the permeability of the polymer to very high levels, but reduce or eliminate the selectivity, as well as adversely affecting the mechanical stability.

For similar reasons, materials having very high fractional free volume of greater than about 0.3 within the polymer itself are not preferred for at least some applications, especially if selectivity is important. In referring to fractional free volume (FFV), we mean the free volume per unit volume of the polymer, defined and calculated as:

$$FFV = SFV/v_{sp}$$

where SFV is the specific free volume, calculated as:

$$SFV = v_{sp} - v_0 = v_{sp} - 1.3 v_w$$

and where:

$v_{sp}$ is the specific volume (cm$^3$/g) of the polymer determined from density or thermal expansion measurements, $v_0$ is the zero point volume at 0°K, and $V_w$ is the van der Waals volume calculated using the group contribution method of Bondi, as described in D. W. van Krevelan, *Properties of Polymers*, 3$^{rd}$ Edition, Elsevier, Amsterdam, 1990, pages 71-76.

Polymers with fractional free volume above 0.3 that should be avoided, at least for some applications, although they otherwise meet the criteria for suitable polymers include perfluoro-2,2-dimethyl-1,3-dioxole copolymers (Teflon®AF polymers).

Preferred polymers for the selective layer of the membrane are formed from highly fluorinated monomers of (i) dioxoles, which are five-member rings of the form that polymerize by opening of the double bond in the ring, so that the ring forms part of the polymer backbone, or (ii) dioxolanes, similar five-member rings but without the double bond in the main ring, or (iii) polymerizable aliphatic structures having an alkyl ether group.

The polymers may be homopolymers of the repeating units of the fluorinated structures defined above. Optionally, they may be copolymers of such repeat units with other polymerizable repeat units. For preference, these other repeat units should be fluorinated, or most preferably perfluorinated.

A number of suitable materials for use in such copolymers are known, for example, fluorinated ethers and ethylene. Particularly when perfluorinated, homopolymers made from these materials, such as polytetrafluoroethylene (PTFE) and the like, are very resistant to swelling by water. However, they tend to be crystalline or semi-crystalline and to have gas permeabilities too low for any useful separation application. As constituents of copolymers with the fluorinated ring structures defined above, however, they can produce materials that combine amorphous structure, good permeability and good resistance to swelling by water. Copolymers that include tetrafluoroethylene units are particularly preferred.

Specific highly preferred materials include copolymers of tetrafluoroethylene with 2,2,4-trifluoro-5-trifluoromethoxy-1,3-dioxole having the structure:

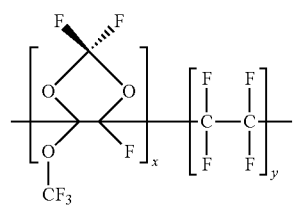

where x and y represent the relative proportions of the dioxole and the tetrafluoroethylene blocks, such that x+y=1.

Such materials are available commercially from Solvay Solexis, Inc. of Thorofare, N.J., under the trade name Hyflon®AD. Different grades are available varying in proportions of the dioxole and tetrafluoroethylene units, with fluorine:carbon ratios of between 1.5 and 2, depending on the mix of repeat units. For example, grade Hyflon®AD 60 contains a 60:40 ratio of dioxole to tetrafluoroethylene units, has a fractional free volume of 0.23 and a glass transition temperature of 121° C., and grade Hyflon®AD 80 contains an 80:20 ratio of dioxole to tetrafluoroethylene units, has a fractional free volume of 0.23 and a glass transition temperature of 134° C.

Other specific highly preferred materials include the set of polyperfluoro (alkenyl vinyl ethers) including polyperfluoro (allyl vinyl ether) and polyperfluoro (butenyl vinyl ether) that are cyclically polymerizable by the formation of repeat units of ether rings with five or six members in the ring.

A particular preferred material of this type has the structure:

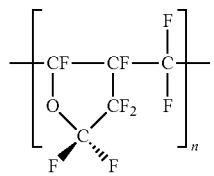

where n is a positive integer.

This material is available commercially from Asahi Glass Company, of Tokyo, Japan under the trade name Cytop®. Cytop® has a fractional free volume of 0.21, a glass transition temperature of 108° C., and a fluorine:carbon ratio of 1.7.

A third group of materials that is believed to contain useful selective layer materials under some circumstances is

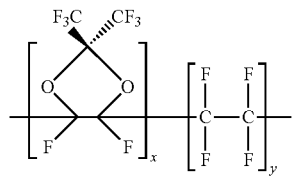

where x and y represent the relative proportions of the dioxole and the tetrafluoroethylene blocks, such that x+y=1.

Such materials are available commercially from DuPont of Wilmington, Del. under the tradename Teflon® AF.

The polymer chosen for the selective layer can be used to form films or membranes by any convenient technique known in the art, and may take diverse forms. Because the polymers are glassy and rigid, an unsupported film, tube or fiber of the polymer is usable as a single-layer membrane.

Single-layer films will normally be too thick to yield acceptable transmembrane flux, however, and, in practice, the separation membrane usually comprises a very thin selective layer that forms part of a thicker structure, such as an integral asymmetric membrane or a composite membrane.

The preferred form is a composite membrane. Modern composite membranes typically comprise a highly permeable but relatively non-selective support membrane, which provides mechanical strength, coated with a thin selective layer of another material that is primarily responsible for the separation properties. Typically, but not necessarily, such a composite membrane is made by solution-casting the support membrane, then solution-coating the selective layer. Preparation techniques for making composite membranes of this type are well known.

Referring to FIG. 1, if the membrane 10 is made in the form of a composite membrane, it is particularly preferred to use a fluorinated or perfluorinated polymer, such as polyvinylidene fluoride (PVDF), to make the microporous support layer 11. The most preferred support layers are those with an asymmetric structure, which provides a smooth, comparatively dense surface on which to coat the selective layer. Support layers are themselves frequently cast onto a backing web of paper or fabric.

The membrane 10 may also include additional layers, such as a gutter layer 12 between the microporous support layer 11 and the selective layer 13, or a sealing layer 14 on top of the selective layer 13. A gutter layer 12 generally has two purposes. The first is to coat the support with a material that seals small defects in the support surface, and itself provides a smooth, essentially defect-free surface onto which the selective layer 13 may be coated. The second is to provide a layer of highly permeable material that can channel permeating molecules to the relatively widely spaced pores in the support layer 11. Preferred materials for the gutter layer 12 are fluorinated or perfluorinated, to maintain high chemical resistance through the membrane structure, and of high permeability. A useful material for the gutter layer is Teflon® AF.

Such materials, or any others of good chemical resistance that provide protection for the selective layer 13 without contributing significant resistance to gas transport, are also suitable as sealing layers 14. The sealing layer 14 will typically be applied over the selective layer(s) 13 to provide protection of the selective layer. Silicone rubber is a useful material for the sealing layer 14.

Multiple selective layers 13 may also be used.

The thickness of the selective layer 13 or skin of the membranes can be chosen according to the proposed use, but will generally be no thicker than 10 μm, and typically no thicker than 5 μm. It is preferred that the selective layer be sufficiently thin that the membrane provide a pressure-normalized flux of the preferentially permeating component, as measured under the operating conditions of the process, of at least about 100 gpu (where 1 gpu=1×10$^{-6}$ cm$^3$(STP)/cm$^2$.s.cmHg), more preferably at least about 500 gpu, and most preferably at least about 1,000 gpu.

It is preferred that the membranes provide a selectivity, as measured with the mixture to be separated and under normal process operating conditions, in favor of water, preferentially permeating component of the mixture, over the organic component from which it is to be separated of at least about 30, and more preferably at least about 50, at least about 100 or higher.

The separation factor provided by the process may be higher or lower than the membrane selectivity, depending on the volatilities of the organic component to be separated under the operating conditions of the process.

The membranes of the invention may be prepared in any known membrane form, such as flat sheets or hollow fibers, and housed in any convenient type of housing and separation unit. We prefer to prepare the membranes in flat-sheet form and to house them in spiral-wound modules. However, flat-sheet membranes may also be mounted in plate-and-frame modules or in any other way. If the membranes are prepared in the form of hollow fibers or tubes, they may be potted in cylindrical housings or otherwise as desired.

The membrane separation unit comprises one or more membrane modules. The number of membrane modules required will vary according to the volume flow of liquid to be treated, the composition of the feed liquid, the desired compositions of the permeate and residue streams, the operating temperature and pressure of the system, and the available membrane area per module.

Systems may contain as few as one membrane module or as many as several hundred or more. The modules may be housed individually in pressure vessels or multiple elements may be mounted together in a sealed housing of appropriate diameter and length.

Figure 2:
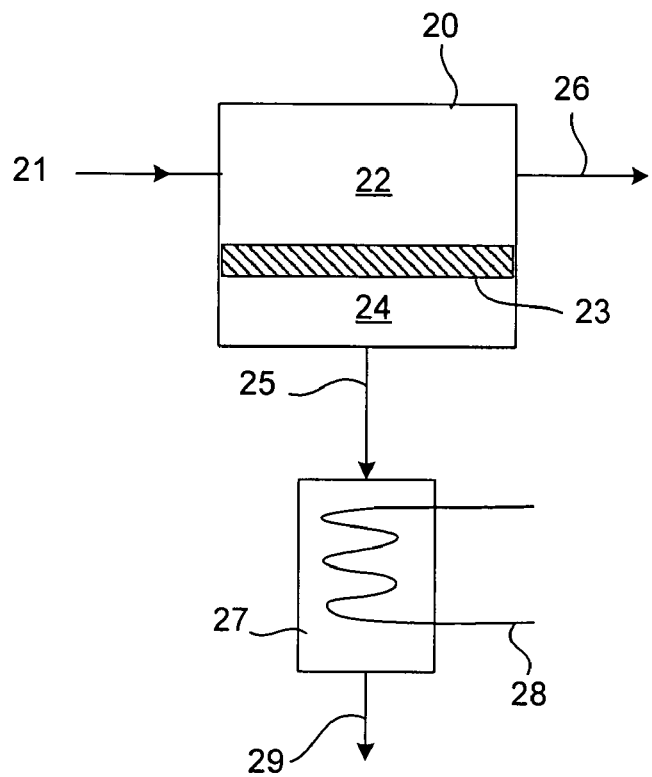
FIG. 2 is a schematic diagram of an embodiment of a system for dehydrating organic/water solutions according to the invention.

One embodiment of apparatus useful for performing the process of the invention is shown in FIG. 2. Referring to this figure, a feedstream 21 comprising a liquid organic/water mixture, is passed into a membrane separation unit 20 and flows across the feed side 22 of membrane 23, which is characterized as described above. Under a vapor pressure difference between the feed 22 and permeate 24 sides of the membrane 23, water passes preferentially to the permeate side 24, and stream 25, enriched in water vapor, is withdrawn in the gas phase from the permeate side 24. The remaining liquid residue stream 26 is withdrawn from the feed side 22. The stream 25 may be condensed in condenser 27 cooled by line 28 containing a coolant to yield a liquid condensate stream 29. The residue stream 26 is withdrawn as the dehydrated product.

Transport through the membrane is induced by maintaining the vapor pressure on the permeate side of the membrane lower than the vapor pressure of the feed liquid. On the feed side of the membrane, the partial vapor pressure of any component will be the partial pressure of the vapor in equilibrium with the feed solution. Changing the hydrostatic pressure of the feed solution thus has a negligible effect on transmembrane flux or selectivity.

However, the vapor pressure on the feed side is a function of the temperature of the feed liquid. If the feed liquid emanates from an operation that is performed at elevated temperature, the feed liquid may already be hot, such as at 70° C., 80° C. or more. If the feed is at a temperature close to, or above, the glass transition temperature of the membrane material, it may be necessary to cool it. Thus, as a general guideline, feed temperatures above 130° C. are not preferred because of their effect on the module component and sometimes the membrane.

On the other hand, if the feed liquid is at a relatively low temperature, such as below about 25° C., it is often desirable to heat the feed liquid to increase the vapor pressure to attain pervaporation conditions, and hence the driving force for permeation. In general, the preferred range of feed temperatures is between about 70° C. and 120° C.

Although changing the hydrostatic pressure on the feed side has little effect, changing the permeate pressure has a major effect on transmembrane flux. The vapor pressure of a component on the permeate side can simply be maintained at atmospheric pressure, or even above atmospheric pressure, if desired. This mode of operation is preferred if the permeating component is to be recovered as a gas or vapor.

Alternatively, the vapor pressure on the permeate side can be reduced in several ways, for example, by drawing a vacuum on the permeate side of the membrane, by sweeping the permeate side to continuously remove permeating vapor, or by cooling the permeate vapor stream to induce condensation. Any such means may be used within the scope of the invention.

If the permeate is to be recovered in liquid form, it is possible simply to cool and condense the permeate stream, thereby generating a partial vacuum on the permeate side. Unless the vapor pressures on the feed side are particularly low (for example, if the feed components are thermally labile and the feed cannot be heated above ambient temperature), this will often suffice to generate adequate driving force, and avoid the cost and operational complexity of a vacuum pump.

Depending on the performance characteristics of the membrane, and the operating parameters of the system, the process can be designed for varying levels of separation. A single-stage pervaporation process typically removes up to about 90-95% of the water from the feed stream. This degree of separation is adequate for many applications.

If the residue stream requires further dehydration, it may be passed to a second bank of modules, after reheating if appropriate, for a second processing step. If the condensed permeate stream requires further concentration, it may be passed to a second bank of modules for a second-stage treatment. Such multistage or multistep processes, and variants thereof, are familiar to those of skill in the art, who will appreciate that the process may be configured in many possible ways, including single-stage, multistage, multistep, or more complicated arrays of two or more units in series or cascade arrangements.

Figure 3:
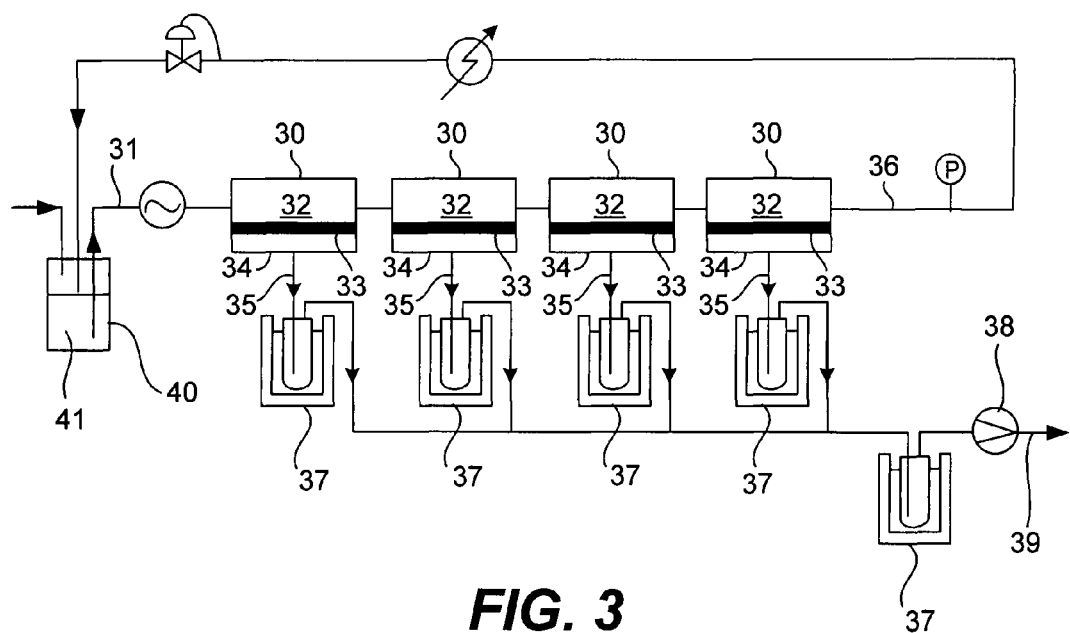
FIG. 3 is another schematic diagram of an embodiment of a system for dehydrating organic/water liquids according to the invention.

A system such as shown in FIG. 3 may be used to evaluate the performance of membrane samples or membrane modules in full recycle test mode as now described. Referring to this figure, a feedstream 31, comprising a liquid organic/water mixture 41, is passed from heated reservoir 40 into one or a plurality of membrane cells or membrane modules 30. The stream flows across the feed side 32 of membrane 33, which is characterized as described above. Under a vapor pressure difference between the feed 32 and permeate 34 sides of the membrane, water passes preferentially to the permeate side 34, and permeate vapor stream 35, enriched in water vapor, is withdrawn in the gas phase from the permeate side. Permeating water and organic compounds are condensed in cold traps 37. A vacuum pump 38 creates a vacuum on the permeate side of the membrane, and withdraws any uncondensed gases through line 39 that may have been dissolved in the feed solution. The condensed permeate collected over a time period is weighed and analyzed. The liquid residue stream 36 is withdrawn from the feed side 32 and recirculated to the feed reservoir 40. The desired test feed composition is maintained by adding fresh water to the reservoir through line 42.

The measured fluxes and concentrations are converted to membrane permeances using the equations $$J_i = \frac{P_i(p_{io} - p_{i\ell})}{\ell}$$

and $$J_j = \frac{P_j(p_{jo} - p_{j\ell})}{\ell}$$

where $J_i$ and $J_j$ are the water and organic component fluxes; $P_i$ and $P_j$ are the water and organic compound permeabilities; l is the membrane thickness; $p_{io}$ and $p_{jo}$ are the feed side water and organic compound vapor pressures; and $p_{i\ell}$ and $p_{j\ell}$ are the permeate side water and organic compound vapor pressures. Since the total permeate pressure $(p_{i\ell}+p_{j\ell})$ is less than 1 mm Hg, these two terms can be set to zero. The feed side partial pressures, $P_{io}$ and $p_{jo}$, are calculated using a process simulator (ChemCAD 5.5, Chemstations, Inc., Houston, Tex.) and an appropriate equation of state. In this way, the permeances $P_i/l$ of water and $P_j/l$ of organic compound can be calculated. The ratio of the permeances $P_i/l/P_j/l$ gives the membrane selectivity $\alpha_{i/j}$.

Figure 4:
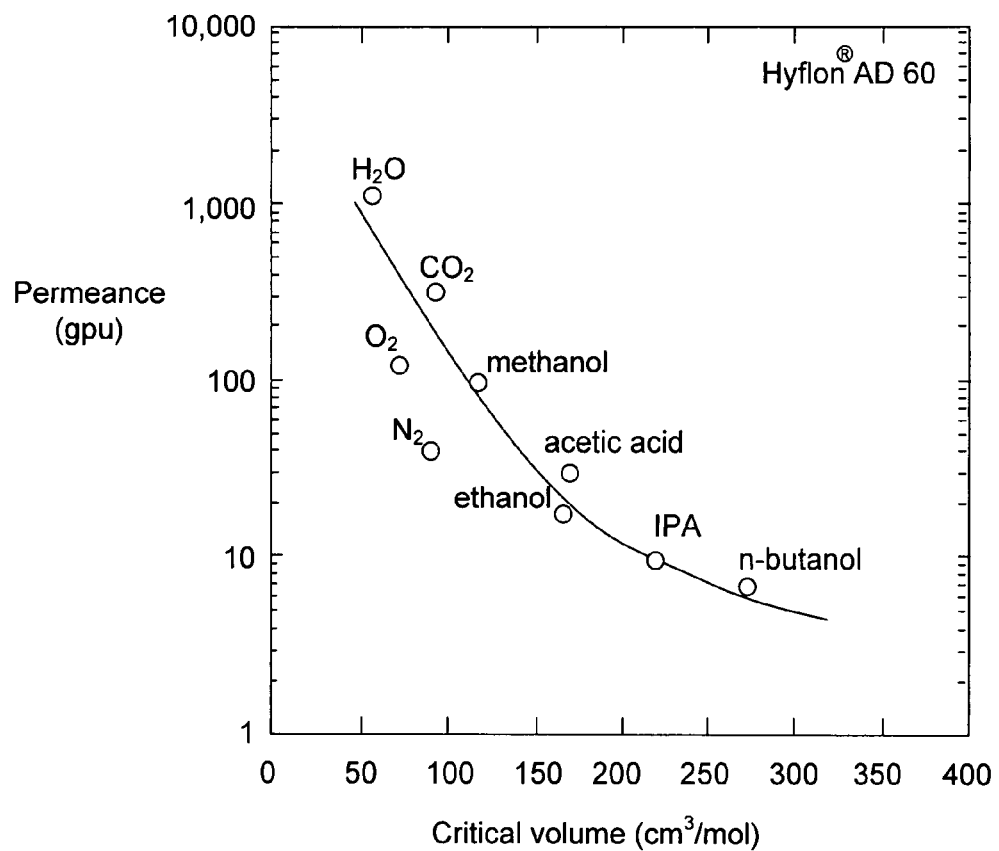
FIG. 4 is a graph of the permeance of several gases and liquids through Hyflon® AD 60 membrane as a function of critical volume.

Representative results obtained with Hyflon®AD 60 perfluoro membranes are shown in Table 1. These results were obtained with large amounts of water in the feed solution. In all cases, the membranes were at least 50-fold more permeable to water than to the organic component. Some of the organic components could hardly be detected in the permeate, indicating a water/organic membrane selectivity of greater than 200. The permeance through a Hyflon®AD membrane decreases as the permeating component size increases, as demonstrated in FIG. 4.

TABLE 1

Performance of Hyflon ® AD 60 Membranes with Feed Solutions containing Water as the Major Component

| Organic Compound | Feed Water Concentration (wt %) | Permeate Water Concentration (wt %) | Water Permeance (gpu) | Organic Compound Permeance (gpu) | Selectivity (water/organic) |
| --- | --- | --- | --- | --- | --- |
| Ethanol | 90.0 | 98.1 | 1,055 | 18 | 59 |
| Isopropanol | 89.6 | 99.9 | 1,166 | 10 | 117 |
| n-Butanol | 95.4 | 99.4 | 1,372 | 7 | 208 |
| Acetic acid | 90.8 | 99.8 | 1,945 | 30 | 65 |

The process of the invention whereby a liquid organic/water feed is supplied to the membrane includes the following steps:

(a) providing a membrane having a feed side and a permeate side, the membrane having a selective layer comprising a polymer with a repeat unit of a hydrophobic fluorinated cyclic structure of an at least 5-member ring;

(b) passing a feed solution comprising at least 1 wt % water and a liquid organic compound across the feed side under pervaporation conditions;

(c) withdrawing from the feed side a dehydrated solution having a water content lower than that of the feed solution;

(d) withdrawing from the permeate side a permeate vapor having a higher water content than the feed solution.

The dehydration process may also be performed in the vapor phase wherein the feed is vaporized and passed through the membrane. In such a process the permeate is collected as a vapor enriched in water vapor and the retentate is collected as a dehydrated vapor. The residue and permeate vapors may optionally be condensed. The driving force for transmembrane permeation may be provided by applying a partial vacuum to the permeate side, pressurizing the feed side or a combination of these techniques.

The process of the invention whereby an organic/water feed vapor is supplied to the membrane includes the following steps:

(a) providing a membrane having a feed side and a permeate side, the membrane having a selective layer comprising a polymer with a repeat unit of a hydrophobic fluorinated cyclic structure of an at least 5-member ring;

(b) passing a feed vapor comprising at least 1 wt % water vapor and a vaporized organic compound across the feed side;

(c) providing a vapor pressure driving force for transmembrane permeation;

(d) withdrawing from the feed side a dehydrated vapor having a water content lower than that of the feed solution;

(e) withdrawing from the permeate side a permeate vapor having a higher water content than the feed solution.

The apparatus design of FIG. 2 may also be used to carry out vapor separation processes. In this case the feedstream 21 is at an elevated temperature, typically above 70° C., and is most preferably compressed to at least about 50 psia to provide a driving force for transmembrane permeation. The feed vapor passes into membrane separation unit 20 and flows across the feed side 22 of membrane 23, which is characterized as described above. Water vapor passes preferentially to the permeate side 24, and stream 25, enriched in water vapor, is withdrawn from the permeate side 24. The residue vapor stream 26 is withdrawn from the feed side 22, and may optionally be condensed. The driving force may be augmented by simply condensing the permeate stream 25 as shown in condenser 27, or by using a vacuum pump instead or as well on the permeate side.

It will often be preferred to either fully or partially condense the permeate vapor stream produced by the processes of the invention. Particularly when the separation is carried out in pervaporation mode, cooling and condensing the permeate will lower the vapor pressure on the permeate side of the membrane and facilitate transmembrane permeation.

Condensation may be carried out in any convenient manner, such as by heat exchange against an external coolant or a plant process stream, for example, as indicated by condenser 27 in FIG. 2. Optionally, the condensation step may be carried out using a dephlegmator, a partial condensation column from which the condensate leaves at the bottom and the uncondensed vapor leaves at the top. The dephlegmator tubes, fins or packing elements behave as wetted walls in which the up-flowing vapor and down-flowing condensate are in countercurrent contact. This provides a separation, improved, for example, four-fold or six-fold compared with that provided by simple condensation.

If a dephlegmation step has been used for other purposes, the processes of the invention can be used to dehydrate either the overhead or bottom stream from the dephlegmator. In fact, it is anticipated that the processes of the invention will often be useful in combination with other separation methods, such as distillation, absorption or adsorption. It will be apparent to those of skill in the art that a pervaporation or vapor separation step in accordance with the invention may be used upstream or downstream of a distillation step, for example.

The membrane separation step may serve a variety of purposes. For example, it may lower the overall volume flow through the distillation column(s), thereby debottlenecking the plant, may provide energy and cost savings by reducing the reboiler duty or the reflux ratio, or may break an azeotrope, rendering one or both of the residue and permeate streams amenable to distillation.

For example, if the overhead stream is such that an azeotrope is formed, the overhead can be condensed, and the condensate subjected to pervaporation, to break the azeotrope. The residue or permeate stream, depending on the nature of the separation, may be withdrawn as a purified product stream, and the other stream may be returned to the appropriate position in the column.

Likewise, the membrane separation step can be used to treat the bottom stream from the distillation column, with the residue or permeate stream forming the purified product, and the other stream being returned to the column. A side cut from the column can also be treated.

The invention is now illustrated in further detail by specific examples. These examples are intended to further clarify the invention, and are not intended to limit the scope in any way.

EXAMPLES

Example 1:

Ethanol dehydration

Figure 5:
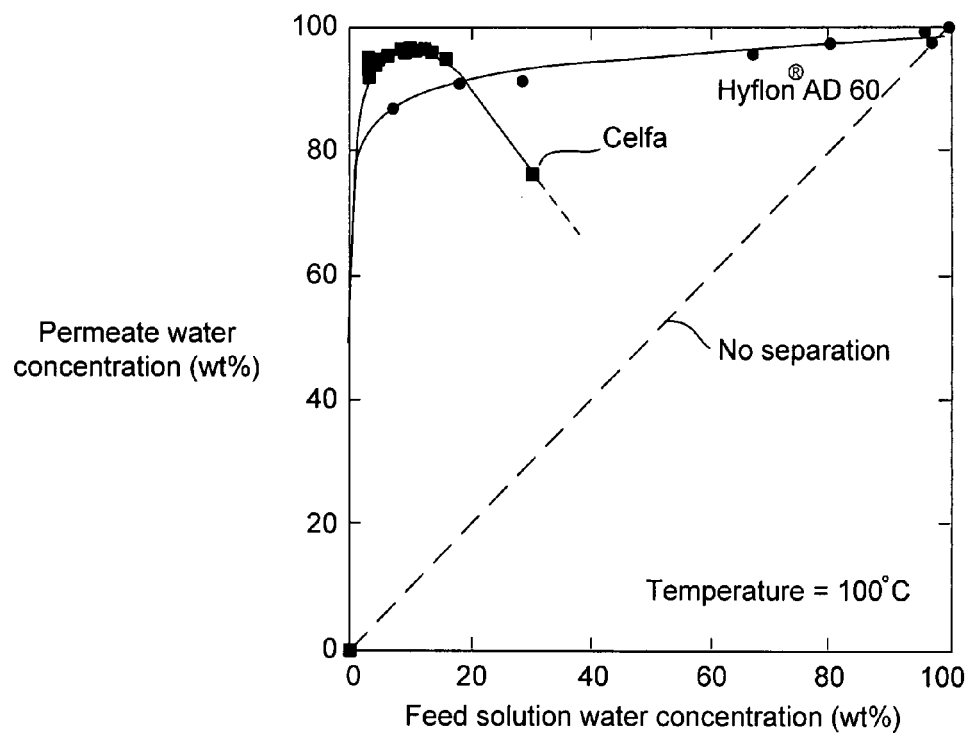
FIG. 5 is a graph comparing the ethanol/water pervaporation separation data of two membranes: Celfa and Hyflon® AD 60, as described in Example 1.
Figure 6:
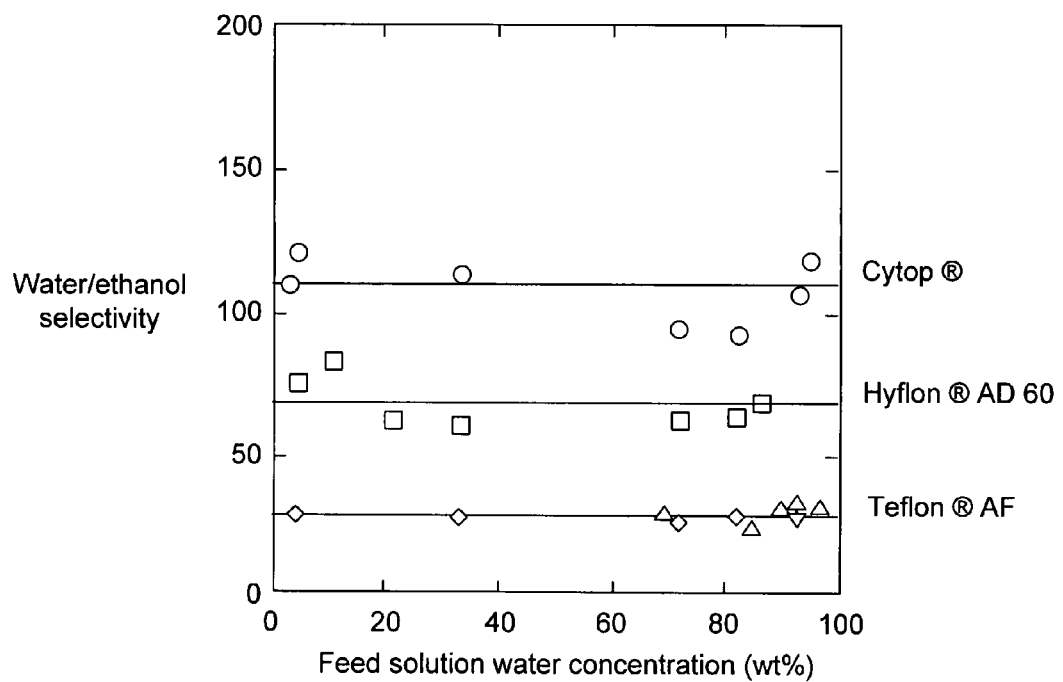
FIG. 6 is a graph showing the ethanol/water selectivities of several perfluoro membranes as described in Example 1.

Three different sets of composite membranes having Hyflon®AD60, Cytop® and Teflon®AF selective layers were prepared by standard casting and coating techniques. For comparison purposes, cross-linked PVA pervaporation membranes were purchases from cm-Celfa Membrantrenntechnik, of Seewen-Schwyz, Switzerland. These membranes are representative of good quality pervaporation membranes in current commercial use. A series of permeation experiments using apparatus similar to that shown in FIG. 3 was carried out with each type of membrane on feed solutions containing various concentrations of water in ethanol. FIG. 5 compares the pervaporation performances of the Hyflon®AD membranes and Celfa membranes for separating ethanol/water mixtures. Perfluoro polymer membranes display good separation performance, regardless of the water concentration in the feed; the permeate water concentration is substantially higher than the feed water concentration across the entire range of water concentration in the feed. Celfa membranes show good separation when the feed water concentration is less than about 10-20 wt %; however, at higher concentrations, the ethanol concentration in the permeate increases abruptly, indicating swelling of the Celfa membrane. This swelling of the membranes in high water content solution does not occur with the Hyflon® AD60 membrane which retains good selectivity for water over ethanol even with water solutions containing up to 95-100 wt % water. FIG. 6 shows comparative results for three membranes made with polymers having a fluorinated ring structure. The water/ethanol selectivities of perfluoro polymer membranes are independent of the feed water concentration from 100% ethanol to 100% water. The selectivity of the Teflon® AF membranes is low compared with the other membrane types.

Example 2

Acetic Acid Dehydration

Figure 7:
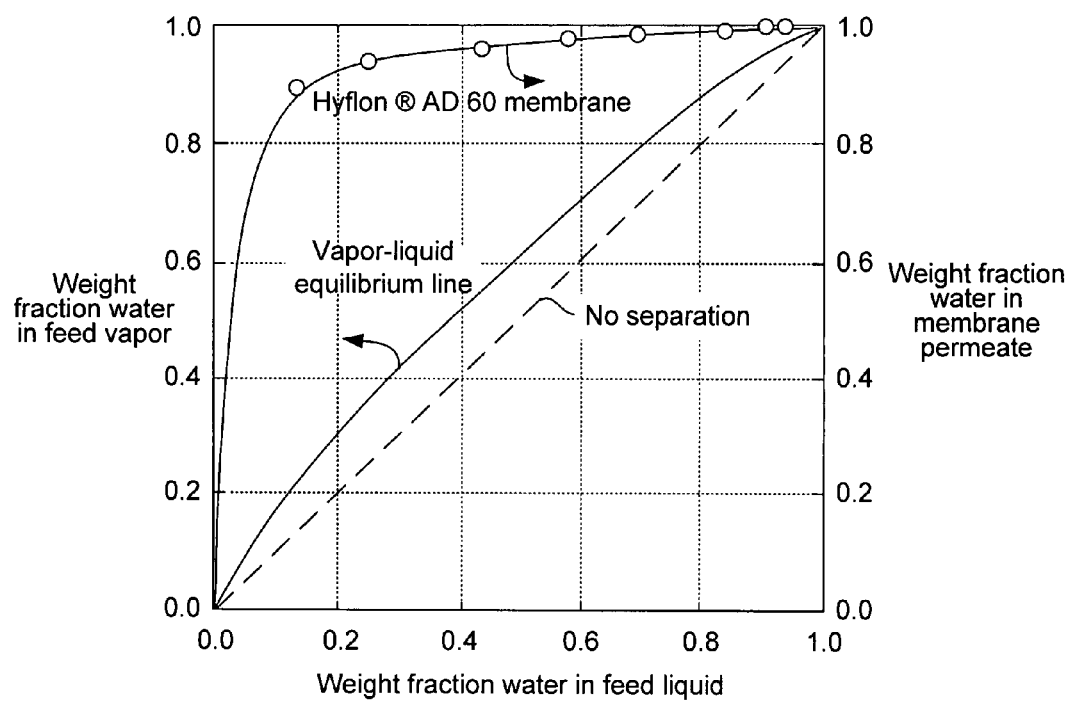
FIG. 7 is a graph comparing the acetic acid/water membrane pervaporation separation data obtained with a Hyflon® AD 60 membrane as described in Example 2.

A set of experiments was performed to evaluate the performance of the Hyflon® AD60 membranes in dehydrating acetic acid. The results are summarized in FIG. 7. As can be seen, the vapor-liquid equilibrium is close to azeotropic over the entire concentration range, making separation by distillation very difficult. In contrast, the membranes are highly selective for water over acetic acid, and can produce a permeate with a very high water concentration even when the feed contains only a small amount of water. As with the ethanol dehydration tests, the membrane performance remains good at high feed water concentrations.

Example 3

Isopropanol Dehydration

Figure 8:
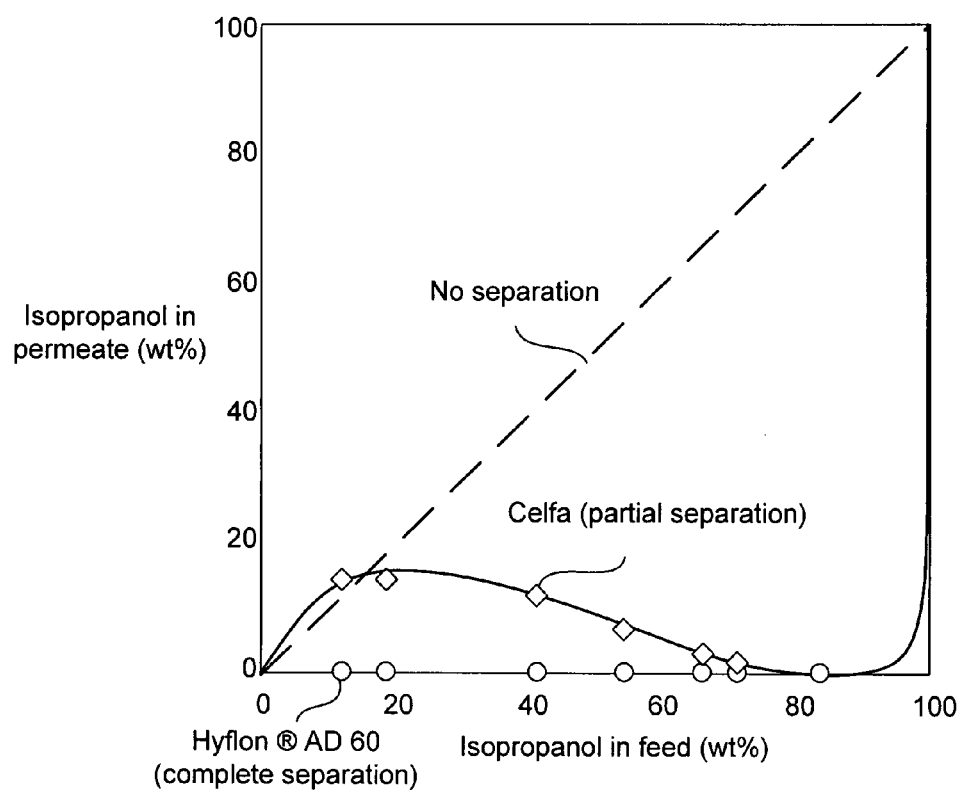
FIG. 8 is a graph comparing the isopropanol/water membrane selectivity of Celfa and Hyflon® AD 60 membranes as described in Example 3.

A set of experiments was performed to evaluate the performance of the Hyflon® AD60 membranes in dehydrating isopropanol. The results are shown in Table 2. In each case, the membrane was able to retain essentially all the isopropanol in the residue and permeate only water, within the limits of accuracy of the equipment. Results using Hyflon®AD60 membranes are compared with results using Celfa crosslinked PVA membranes in FIG. 8. As can be seen by the absence of isopropanol in the permeate, the Celfa membranes provide good separation performance down to about 80 wt % isopropanol. At lower isopropanol concentration (higher water concentration) in the feed solution, the separation performance declines and increasingly large amounts of isopropanol permeate the membrane. In contrast, the Hyflon®AD membranes provide complete separation at all water concentrations.

TABLE 2

Pervaporation of Isopropanol/Water Mixtures through a Hyflon ® AD60 Composite Membrane.
Temperature: 75° C.; permeate pressure: <5 torr.

| Feed Concentration (wt % Water) | Permeate Concentration (wt % Water)$^a$ | Membrane Flux (kg/m$^2$h) | Water Permeance (gpu) |
|---|---|---|---|
| 16.7 | >99.7 | 1.0 | 1,580 |
| 29.2 | >99.7 | 1.1 | 1,420 |
| 34.3 | >99.7 | 1.2 | 1,550 |
| 46.3 | >99.7 | 1.2 | 1,530 |
| 59.3 | >99.7 | 1.1 | 1,450 |
| 81.5 | >99.7 | 1.1 | 1,360 |
| 88.2 | >99.7 | 1.3 | 1,580 |

$^a$Permeate concentration measured for each run was >99.7%, the maximum measurable level.

Example 4

Butanol Dehydration

A set of experiments was performed to compare the performance of Hyflon®AD60 membranes and Celfa crosslinked PVA membranes in dehydrating solutions of n-butanol and ethanol containing 30 wt % water. The results are summarized in Table 3. As can be seen, the Hyflon®AD60 membranes had better separation performance in both cases than the Celfa PVA membranes.

TABLE 3

Dehydration Performance of Hyflon ® AD60 and Celfa Membranes with Water/Organic Mixtures containing 30 wt % Water at 75° C.

| | Water Concentration in Permeate (wt %) | |
|---|---|---|
| Organic compound | Celfa PVA Membrane | Hyflon ® AD60 Membrane |
| Ethanol | 76.3 | 93.2 |
| n-Butanol | 68.4 | 95.3 |

What is claimed is:
1. A dehydration process, comprising:
(a) providing a membrane having a feed side and a permeate side wherein said membrane is selectively permeable to water over organic compounds, the membrane having a selective layer comprising a polymer with a repeat unit of a hydrophobic fluorinated cyclic structure of an at least 5-member ring;
(b) passing a feed solution comprising at least 1 wt % water and a liquid organic compound across the feed side under pervaporation conditions;
(c) withdrawing from the feed side a dehydrated solution having a water content lower than that of the feed solution;
(d) withdrawing from the permeate side a permeate vapor having a higher water content than the feed solution.

2. A dehydration process, comprising:
(a) providing a membrane having a feed side and a permeate side wherein said membrane is selectively permeable to water over organic compounds, the membrane having a selective layer comprising a polymer with a repeat unit of a hydrophobic fluorinated cyclic structure of an at least 5-member ring;
(b) passing a feed vapor comprising at least 1 wt % water vapor and a vaporized organic compound across the feed side;
(c) providing a vapor pressure driving force for transmembrane permeation;
(d) withdrawing from the feed side a dehydrated vapor having a water content lower than that of the feed solution;
(e) withdrawing from the permeate side a permeate vapor having a higher water content than the feed solution.

3. The process of claim 1 or 2, wherein the polymer is sufficiently stable in the presence of water that a film of the polymer immersed in water at 100° C. for 24 hours at atmospheric pressure experiences a weight change of no more than about 10 wt % after immersion.

4. The process of claim 1 or 2, wherein said polymer is formed from a monomer selected from the group consisting of fluorinated dioxoles, fluorinated dioxolanes and fluorinated cyclically polymerizable alkyl ethers.

5. The process of claim 1 or 2, wherein said polymer comprises a perfluorinated polymer.

6. The process of claim 1 or 2, wherein the polymer has the formula:

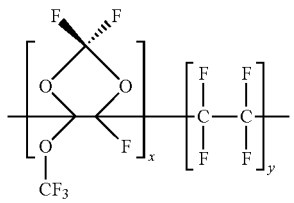

where x and y represent the relative proportions of the dioxole and the tetrafluoroethylene blocks, such that x+y=1.

7. The process of claim 1 or 2, wherein said polymer has the formula:

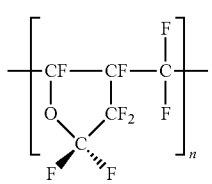

where n is a positive integer.

8. The process of claim 1 or 2 wherein said polymer has the formula

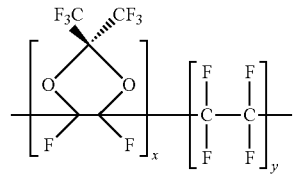

where x and y represent the relative proportions of the dioxole and the tetrafluoroethylene blocks, such that x+y=1.

9. The process of claim 1 or 2, wherein said polymer has a ratio of fluorine to carbon atoms of at least about 1:1.

10. The process of claim 1 or 2, wherein said membrane comprises a composite membrane.

11. The process of claim 1 or 2, further comprising condensing at least a portion of the permeate vapor.

12. The process of claim 1 or 2, further comprising passing at least a portion of a stream chosen from the permeate vapor, the dehydrated solution and the dehydrated vapor to additional separation treatment.

13. The process of claim 2, further comprising the step of condensing at least a portion of the dehydrated vapor.

14. The process of claim 1 or 2, wherein said organic compound comprises a C1-C6 alcohol.

15. The process of claim 1 or 2, wherein said organic compound comprises an ester.

16. The process of claim 1 or 2, wherein said organic compound comprises an acid.

17. The process of claim 1 or 2, wherein said organic compound comprises an aldehyde or a ketone.

18. The process of claim 14, wherein said alcohol is selected from the group consisting of ethanol, isopropanol and butanol.

19. The process of claim 16, wherein said acid is acetic acid.

20. The process of claim 18, wherein said ethanol is a product of bioethanol production.

21. The process of claim 1, wherein said pervaporation conditions in step (b) include providing said feed solution to said membrane at a temperature in the range of about 70-120° C.

22. The process of claim 2, wherein said water vapor and vaporized organic compound are provided to said membrane in step (b) at a temperature above about 70° C.

23. The process of claim 1 or 2, wherein the water solubility in said organic compound is above about 10 wt % water.

24. The process of claim 2, wherein said driving force in step (c) is provided by applying pressure to said feed vapor on said feed side.

25. The process of claim 2, wherein said driving force in step (c) is provided by applying a partial vacuum to said permeate side.

26. The process of claim 1 or 2, wherein said membrane is further characterized in that it provides a membrane selectivity of water to the organic compound of at least about 30 and a water permeance of at least about 500 gpu when challenged at 75° C. with a liquid mixture of 10 wt % water/90 wt % ethanol at a permeate pressure of 10 torr.

* * * * *